US00PP07893P

United States Patent [19]

Nielsen

[11] Patent Number: Plant 7,893

[45] Date of Patent: Jun. 23, 1992

[54] *FICUS BENJAMINA* L. NAMED 'CHRISTINE'

[75] Inventor: Svend Nielsen, Tommerup, Denmark

[73] Assignees: L. Daehnfeldt, Ltd., Odense, Denmark; Tropical Foliage House, Homestead, Fla.

[21] Appl. No.: 514,400

[22] Filed: Apr. 26, 1990

[51] Int. Cl.[5] ..... A01H 5/00

[52] U.S. Cl. ..... Plt./88

[58] Field of Search ..... Plt./88

[56] References Cited

PUBLICATIONS

Bailey, L. H. "Ficus:13. Benjamina" *The Standard Cyclopedia of Horticulture, The MacMillan Co., N.Y., 1943 p. 1232.*

Weiner, M. A. "FIG, Benjamin" Plant A Tree, Collier Books, N.Y. 1975, pp. 168 and 171.

Herwig, R. "Ficus" *Healthy House Plants*, H.P. Books, Tucson, Ariz., 1979, p. 77.

Graf, A. B. "Ficus" *Exotica* Roehrs Company, Rutherford, N.Y., U.S.A., 1963, p. 1614.

*Primary Examiner*—James R. Feyrer

*Attorney, Agent, or Firm*—Malloy, Downey & Malloy

[57] ABSTRACT

The present invention is directed to a sport of *Ficus benjamina* L., 'Exotica' and is characterized by an exceptionally compact habit, with small leaves, and short internodes. The new cultivar is known as *Ficus benjamina* L. 'Christine' and is especially suited for pot-plant production.

1 Drawing Sheet

BACKGROUND OF THE INVENTION

Field of the Invention

The present invention relates to a new distinct variety of ficus plants known botanically as *Ficus benjamina*, the new variety being known by the cultivar mane of *Ficus benjamina* L. 'Christine', and being characterized by its exeptionally compact size and small leaves.

DESCRIPTION OF THE REALTED ART

The present variety of the new cultivar of the present invention is known as *Ficus benjamina* L. 'Exotica' and is generally a large, outdoor plant which, due to its size, is ordinarly grown in the ground. Existing Fisus plans including 'Exotica' are not generally suited for pot-production.

SUMMARY OF THE INVENTION

The present new cultivar *Ficus benjamina* L. 'Christine' is a result of a "bud sport" mutation found in 1988 in a batch of greenhouse-grown weeping *Ficus benjamina* L. 'Exotica' in my nursery in Denmark. The mutation has been asexually propagated, first by meristem culture and thereafter by cuttings through several generations to secure consistency in type and growth habit. The goal is to make this a perfect foliage plant for pot-production.

Descriptions and measurements were carried out on Jun. 28, 1991, and the color reading is based on *The Royal Horticultural Society'Colour Chart.*

*Ficus benjamnla* L. 'Christine' is a new variety of Ficus being consistant in size and distinguished clearly from its parent, *Ficus benjamina* 'Exotica' and other known cultivars by the following:

A. Compact growth with an average internode length of 19 mm. compared with the parent cultivar 'Exotica' of 41 mm. Measured on the two types grown together in a 13 cm. pot to a height of 50 cm.

B. The leaf lamina length is 52 mm. compared with "Exotica" having a length of 80 mm.

The leaf width 21 mm. compared with 'Exotica' 33 mm. The ratio length/width is similar for both cultivars, being 2.5:1.

C. The life-length of the bottom leaves are very persistent. New leaves have a concave character.

BRIEF DESCRIPTION OF THE VARIOUS FIGURES OF THE DRAWINGS

The accompanying photographs and drawing illustrate the morphology and difference in size between 'Christine' and the parent variety 'Exotica' and is based on plants grown under the same conditions in which:

The top figure of the drawing depicts a typical specimen of the claimed plant 'Christine' on the left and a comparably grown specimen of the parent variety 'Exotica' on the right to illustrate the dramatic differences in size and compactness of the two plants;

The middle figure of the drawing depicts, in close perspective, the bark, lentilces, typical branch spacing, branch angles, internodes, and leaves of the claimed plant; and, The bottom figure of the drawing shows a typical leaf of about average size of the claimed plant 'Christine' on the left, and a typical leaf of about average size of the parent plant 'Exotica' on the right, and shows the similar shape and coloration of the leaves of each plant.

BOTANICAL DESCRIPTION

Plant

Origin: Bud-mutation and successive selections in asexually propagated material.

Form: Upright with strong development of side twigs from base to terminal buds.

Height: 25 cm., grown for 16 weeks in 9 cm. pot as multi-stemmed.

Diameter: 28 cm., grown for 16 weeks in 9 cm. pot.

Growth rate: Rather slow, producing a sturdy plant.

Type of cuttings: Semi-mature top and side shoots.

Rooting Time: 18–21 days.

Rooting habit: Dense and Fibrous

Twigs: Sideshoot of 10 c.m. have a thickness of 2.5 mm. Appearing alternate on main stems with an average distance of 18 mm. (from bottom to top of a 40 cm. plant).

Internode: 11–18 mm.

Bark: Young twigs bars are glabrous, green, HCC 148B. Semi-mature twigs are brown with a thin cover of longitudinal stripes of shedding epidermis. Mature stems are brown, HCC 199B, with small scattered lenticells.

Buds: New growth arrive from alternate, auxillary, terminal buds in a zigzag pattern. pattern. Color: light green, HCC 144 B. No stipules (leaf scales). Dormant buds are thin, pin-like, green of 5–8 mm. length.

Foliage

Arrangements: Alternate with a phyllotaxi of 5.

Shape of Leaves: Elliptic-ovate, subrounded at base, acuminate with a 8–10 mm. leaf-tip.

Leaf Canopy: Leaves present right from bottom to top.

Margin: Entire.

Venation: Medium size mid-rib, light green, HCC 144 C. lamina with close, fine pinnates extending to margin.

Size: Average length of lamine (without petiole) 52 mm. Average width: 21 mm.

Surface: Smooth.

Texture: Glabrous, shiny.

Variegation: None

Leaf color: Upper side HCC 144 A (young leaves) Ventral (underside) HCC 144 B (young leaves) Upper side HCC 139 A (old leaves) Ventral HCC 137 B (old leaves) Leaves exposed to sun: Upper side HCC 144 B.

Hydathodes: Minute, scattered along edges of upper side.

Petioles: Length 9–10 mm., color green HCC 144 B.

Form of lamina: Young leaves concave.

Flower and fruiting: Very rarely seen on greenhouse plants.

Growth rate: Rather slow to produce a sturdy compact plant.

Having thus disclosed my presentation, I claim:

1. A new and distinct variety of *Ficus benjamina* L. plant named 'Christine', substantially as shown and described, characterized as a very compact, small leaved Ficus especially suited for pot-plant culture, the cultivar having proved to be constant through several generations of asexually propagated material, wherein the compactness, number of small leaves and short internodes distinguish 'Christine' clearly from the parent plant, *Ficus benjamina* L. 'Exotica'.

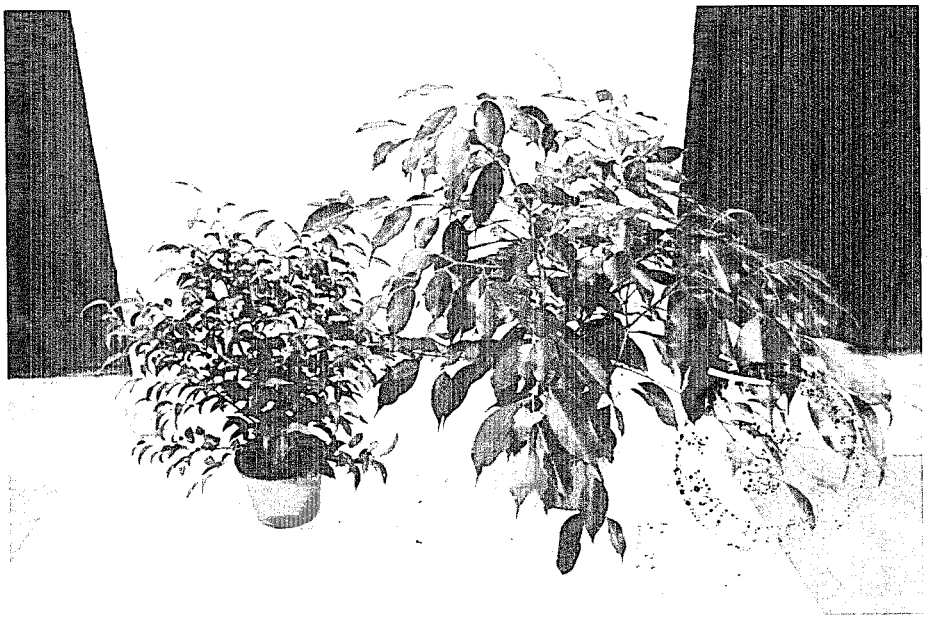
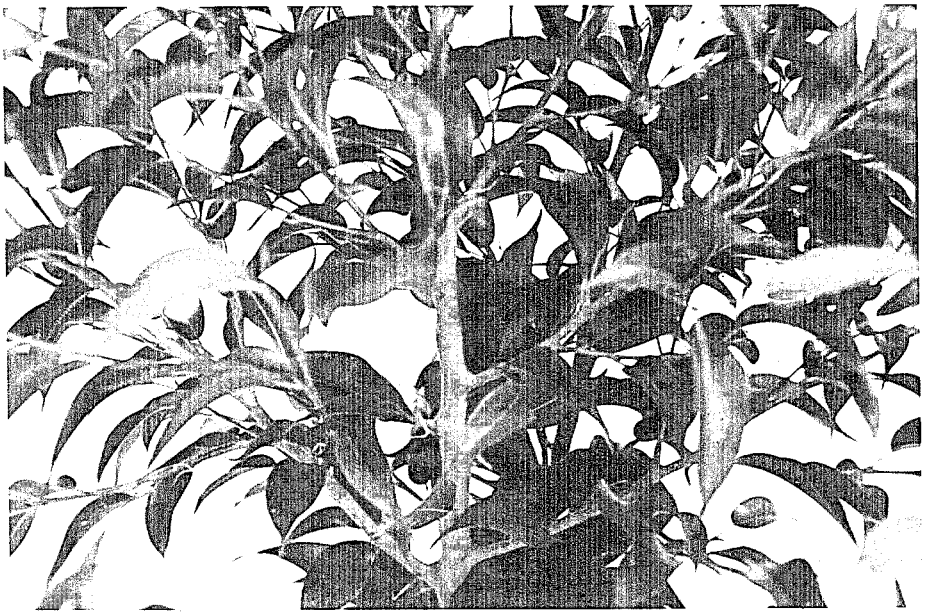
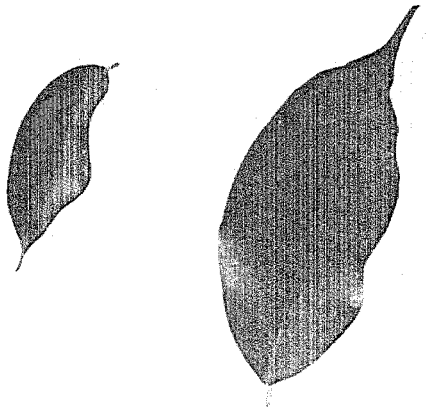

* * * * *